(12) United States Patent
Osborne

(10) Patent No.: US 8,246,672 B2
(45) Date of Patent: Aug. 21, 2012

(54) ENDOVASCULAR GRAFT WITH SEPARATELY POSITIONABLE AND REMOVABLE FRAME UNITS

(75) Inventor: Thomas A. Osborne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 531 days.

(21) Appl. No.: 12/339,596

(22) Filed: Dec. 19, 2008

(65) Prior Publication Data

US 2009/0171441 A1 Jul. 2, 2009

Related U.S. Application Data

(60) Provisional application No. 61/017,051, filed on Dec. 27, 2007.

(51) Int. Cl.
*A61F 2/06* (2006.01)
(52) U.S. Cl. ........................ 623/1.13; 623/1.16
(58) Field of Classification Search ............... 623/1.13, 623/1.23, 1.36, 1.16
See application file for complete search history.

(56) References Cited

U.S. PATENT DOCUMENTS

| | | | |
|---|---|---|---|
| 2,281,448 A | 4/1942 | Mathey |
| 3,137,298 A | 6/1964 | Glassman |
| 3,174,851 A | 3/1965 | Buehler |
| 3,334,629 A | 8/1967 | Cohn |
| 3,540,431 A | 11/1970 | Mobin-Uddin |
| 3,868,956 A | 3/1975 | Alfidi et al. |
| 3,952,747 A | 4/1976 | Kimmell, Jr. |
| 4,425,908 A | 1/1984 | Simon |
| 4,494,531 A | 1/1985 | Gianturco |
| 4,619,246 A | 10/1986 | Molgaard-Nielsen et al. |
| 4,643,184 A | 2/1987 | Mobin-Uddin |
| 4,655,771 A | 4/1987 | Wallsten |
| 4,665,906 A | 5/1987 | Jervis |
| 4,688,553 A | 8/1987 | Metals |
| 4,727,873 A | 3/1988 | Mobin-Uddin |
| 4,759,757 A | 7/1988 | Pinchuk |
| 4,781,177 A | 11/1988 | Lebigot |
| 4,793,348 A | 12/1988 | Palmaz |
| 4,817,600 A | 4/1989 | Herms et al. |
| 4,830,003 A | 5/1989 | Wolff et al. |
| 4,832,055 A | 5/1989 | Palestrant |
| 4,856,516 A | 8/1989 | Hillstead |
| 4,873,978 A | 10/1989 | Ginsburg |
| 4,943,297 A | 7/1990 | Saveliev et al. |
| 4,950,227 A | 8/1990 | Savin et al. |

(Continued)

FOREIGN PATENT DOCUMENTS

DE 003417738 11/1985

(Continued)

OTHER PUBLICATIONS

International Search Report—PCT/US2005/013158 (Oct. 7, 2005).

(Continued)

*Primary Examiner* — William H. Matthews
(74) *Attorney, Agent, or Firm* — Brinks Hofer Gilson & Lione

(57) ABSTRACT

A device for repairing a vessel body including a plurality distinct and independently positionable, expandable frame units disposed within a tubular graft. The independent frame units are capable of being positioned, repositioned, or removed to conform the tubular graft to the anatomy of the vessel body.

18 Claims, 11 Drawing Sheets

U.S. PATENT DOCUMENTS

| | | |
|---|---|---|
| 4,954,126 A | 9/1990 | Wallsten |
| 4,957,501 A | 9/1990 | Lahille et al. |
| 4,969,891 A | 11/1990 | Gewertz |
| 4,990,156 A | 2/1991 | Lefebvre |
| 5,037,377 A | 8/1991 | Alonso |
| 5,059,205 A | 10/1991 | El-Nounou et al. |
| 5,061,275 A | 10/1991 | Wallsten et al. |
| 5,067,957 A | 11/1991 | Jervis |
| 5,071,407 A | 12/1991 | Termin et al. |
| 5,108,418 A | 4/1992 | Lefebvre |
| 5,108,419 A | 4/1992 | Reger et al. |
| 5,133,733 A | 7/1992 | Rasmussen et al. |
| 5,135,516 A | 8/1992 | Sahatjian et al. |
| 5,147,379 A | 9/1992 | Sabbaghian et al. |
| 5,152,777 A | 10/1992 | Goldberg et al. |
| 5,160,342 A | 11/1992 | Reger et al. |
| 5,190,546 A | 3/1993 | Jervis |
| 5,217,484 A | 6/1993 | Marks |
| 5,221,261 A | 6/1993 | Termin et al. |
| 5,224,953 A | 7/1993 | Morgentaler |
| 5,234,458 A | 8/1993 | Metais |
| 5,242,462 A | 9/1993 | El-Nounou et al. |
| 5,300,086 A | 4/1994 | Gory et al. |
| 5,304,121 A | 4/1994 | Sahatjian |
| 5,304,200 A | 4/1994 | Spaulding |
| 5,324,304 A | 6/1994 | Rasmussen |
| 5,329,942 A | 7/1994 | Gunther et al. |
| 5,344,427 A | 9/1994 | Cottenceau et al. |
| 5,350,398 A | 9/1994 | Pavcnik et al. |
| 5,370,657 A | 12/1994 | Irie |
| 5,375,612 A | 12/1994 | Cottenceau et al. |
| 5,382,261 A | 1/1995 | Palmaz |
| 5,383,887 A | 1/1995 | Nadal |
| 5,405,377 A | 4/1995 | Cragg |
| 5,413,586 A | 5/1995 | Dibie et al. |
| 5,421,832 A | 6/1995 | Lefebvre |
| 5,476,508 A | 12/1995 | Amstrup |
| 5,527,338 A | 6/1996 | Purdy |
| 5,540,712 A | 7/1996 | Kleshinski et al. |
| 5,549,626 A | 8/1996 | Miller et al. |
| 5,549,629 A | 8/1996 | Thomas et al. |
| 5,601,595 A | 2/1997 | Smith |
| 5,626,605 A | 5/1997 | Irie et al. |
| 5,630,801 A | 5/1997 | Roussigne et al. |
| 5,634,942 A | 6/1997 | Chevillon et al. |
| 5,649,906 A | 7/1997 | Gory et al. |
| 5,649,953 A | 7/1997 | Lefebvre |
| 5,669,933 A | 9/1997 | Simon et al. |
| 5,681,347 A | 10/1997 | Cathcart et al. |
| 5,683,411 A | 11/1997 | Kavteladze et al. |
| 5,695,519 A | 12/1997 | Summers et al. |
| 5,709,704 A | 1/1998 | Nott et al. |
| 5,720,764 A | 2/1998 | Naderlinger |
| 5,725,550 A | 3/1998 | Nadal |
| 5,746,767 A | 5/1998 | Smith |
| 5,755,778 A | 5/1998 | Kleshinski |
| 5,755,790 A | 5/1998 | Chevillon et al. |
| 5,776,162 A | 7/1998 | Kleshinski |
| 5,800,457 A | 9/1998 | Gelbfish |
| 5,800,525 A | 9/1998 | Bachinski et al. |
| 5,807,398 A | 9/1998 | Shaknovich |
| 5,810,874 A | 9/1998 | Lefebvre |
| 5,836,968 A | 11/1998 | Simon et al. |
| 5,836,969 A | 11/1998 | Kim et al. |
| 5,843,244 A | 12/1998 | Pelton et al. |
| 5,853,420 A | 12/1998 | Chevillon et al. |
| 5,895,399 A | 4/1999 | Barbut et al. |
| 5,902,317 A | 5/1999 | Kleshinski et al. |
| 5,916,235 A | 6/1999 | Guglielmi |
| 5,928,260 A | 7/1999 | Chin et al. |
| 5,928,261 A | 7/1999 | Ruiz |
| 5,932,035 A | 8/1999 | Koger et al. |
| 5,938,683 A | 8/1999 | Lefebvre |
| 5,951,585 A | 9/1999 | Cathcart et al. |
| 5,961,546 A | 10/1999 | Robinson et al. |
| 5,976,172 A | 11/1999 | Homsma et al. |
| 5,984,947 A | 11/1999 | Smith |
| 6,007,557 A | 12/1999 | Ambrisco et al. |
| 6,007,558 A | 12/1999 | Ravenscroft et al. |
| 6,013,093 A | 1/2000 | Nott et al. |
| 6,077,274 A | 6/2000 | Ouchi et al. |
| 6,080,178 A | 6/2000 | Meglin |
| 6,086,610 A | 7/2000 | Duerig et al. |
| 6,126,673 A | 10/2000 | Kim et al. |
| 6,129,755 A | 10/2000 | Mathis et al. |
| 6,146,404 A | 11/2000 | Kim et al. |
| 6,152,144 A | 11/2000 | Lesh et al. |
| 6,152,956 A * | 11/2000 | Pierce .......................... 623/1.13 |
| 6,156,055 A | 12/2000 | Ravenscroft |
| 6,156,061 A | 12/2000 | Wallace et al. |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,193,739 B1 | 2/2001 | Chevillon et al. |
| 6,221,102 B1 | 4/2001 | Baker et al. |
| 6,231,589 B1 | 5/2001 | Wessman et al. |
| 6,241,738 B1 | 6/2001 | Dereume |
| 6,241,746 B1 | 6/2001 | Bosma et al. |
| 6,245,012 B1 | 6/2001 | Kleshinski |
| 6,245,088 B1 | 6/2001 | Lowery |
| 6,251,122 B1 | 6/2001 | Tsukernik |
| 6,258,026 B1 | 7/2001 | Ravenscroft et al. |
| 6,267,776 B1 | 7/2001 | O'Connell |
| 6,273,900 B1 | 8/2001 | Nott et al. |
| 6,273,901 B1 | 8/2001 | Whitcher et al. |
| 6,277,139 B1 | 8/2001 | Levinson et al. |
| 6,280,467 B1 * | 8/2001 | Leonhardt ................... 623/1.16 |
| 6,287,315 B1 | 9/2001 | Wijeratne et al. |
| 6,287,329 B1 | 9/2001 | Duerig et al. |
| 6,306,163 B1 | 10/2001 | Fitz |
| 6,312,454 B1 | 11/2001 | Stockel et al. |
| 6,312,455 B2 | 11/2001 | Duerig et al. |
| 6,325,815 B1 | 12/2001 | Kusleika et al. |
| 6,331,183 B1 | 12/2001 | Suon |
| 6,342,062 B1 | 1/2002 | Suon et al. |
| 6,342,063 B1 | 1/2002 | DeVries et al. |
| 6,342,067 B1 | 1/2002 | Mathis et al. |
| 6,346,116 B1 | 2/2002 | Brooks et al. |
| 6,364,895 B1 | 4/2002 | Greenhalgh |
| 6,391,044 B1 | 5/2002 | Yadav et al. |
| 6,391,045 B1 | 5/2002 | Kim et al. |
| 6,436,120 B1 | 8/2002 | Meglin |
| 6,436,121 B1 | 8/2002 | Blom |
| 6,447,530 B1 | 9/2002 | Ostrovsky et al. |
| 6,461,370 B1 | 10/2002 | Gray et al. |
| 6,468,290 B1 | 10/2002 | Weldon et al. |
| 6,482,222 B1 | 11/2002 | Bruckheimer et al. |
| 6,485,502 B2 | 11/2002 | DonMichael et al. |
| 6,506,205 B2 | 1/2003 | Goldberg et al. |
| 6,511,503 B1 | 1/2003 | Burkett et al. |
| 6,517,559 B1 | 2/2003 | O'Connell |
| 6,527,962 B1 | 3/2003 | Nadal |
| 6,540,767 B1 | 4/2003 | Walak et al. |
| 6,551,342 B1 | 4/2003 | Shen et al. |
| 6,558,404 B2 | 5/2003 | Tsukernik |
| 6,569,183 B1 | 5/2003 | Kim et al. |
| 6,579,303 B2 | 6/2003 | Amplatz |
| 6,582,447 B1 | 6/2003 | Patel et al. |
| 6,589,266 B2 | 7/2003 | Whitcher et al. |
| 6,602,226 B1 | 8/2003 | Smith et al. |
| 6,616,680 B1 | 9/2003 | Thielen |
| 6,638,294 B1 | 10/2003 | Palmer |
| 6,652,558 B2 | 11/2003 | Patel et al. |
| 6,685,722 B1 | 2/2004 | Rosenbluth et al. |
| 7,297,000 B1 | 11/2007 | Bernard |
| 2001/0000799 A1 | 5/2001 | Wessman et al. |
| 2001/0011181 A1 | 8/2001 | DiMatteo |
| 2001/0023358 A1 | 9/2001 | Tsukernik |
| 2001/0034547 A1 | 10/2001 | Hall et al. |
| 2001/0034548 A1 | 10/2001 | Vrba et al. |
| 2001/0037126 A1 | 11/2001 | Stack et al. |
| 2001/0039432 A1 | 11/2001 | Whitcher et al. |
| 2002/0002401 A1 | 1/2002 | McGuckin, Jr. et al. |
| 2002/0016624 A1 | 2/2002 | Patterson et al. |
| 2002/0032460 A1 | 3/2002 | Kusleika et al. |
| 2002/0039445 A1 | 4/2002 | Abe et al. |
| 2002/0055767 A1 | 5/2002 | Forde et al. |

| | | |
|---|---|---|
| 2002/0087187 A1 | 7/2002 | Mazzocchi et al. |
| 2002/0099431 A1 | 7/2002 | Armstrong et al. |
| 2002/0116024 A1 | 8/2002 | Goldberg et al. |
| 2002/0133217 A1 | 9/2002 | Sirhan et al. |
| 2002/0138097 A1 | 9/2002 | Ostrovsky et al. |
| 2002/0156520 A1 | 10/2002 | Boylan et al. |
| 2002/0161393 A1 | 10/2002 | Demond et al. |
| 2002/0169474 A1 | 11/2002 | Kusleika et al. |
| 2002/0169495 A1 | 11/2002 | Gifford et al. |
| 2002/0183782 A1 | 12/2002 | Tsugita et al. |
| 2002/0193827 A1 | 12/2002 | McGuckin, Jr. et al. |
| 2002/0193828 A1 | 12/2002 | Griffin et al. |
| 2002/0193874 A1 | 12/2002 | Crowley |
| 2003/0018343 A1 | 1/2003 | Mathis |
| 2003/0028238 A1 | 2/2003 | Burkett et al. |
| 2003/0040772 A1 | 2/2003 | Hyodoh et al. |
| 2003/0055481 A1 | 3/2003 | McMorrow |
| 2003/0069596 A1 | 4/2003 | Eskuri |
| 2003/0074019 A1 | 4/2003 | Gray et al. |
| 2003/0078614 A1 | 4/2003 | Salahieh et al. |
| 2003/0083692 A1 | 5/2003 | Vrba et al. |
| 2003/0097145 A1 | 5/2003 | Goldberg et al. |
| 2003/0105484 A1 | 6/2003 | Boyle et al. |
| 2003/0109897 A1 | 6/2003 | Walak et al. |
| 2003/0114880 A1 | 6/2003 | Hansen et al. |
| 2003/0125790 A1 | 7/2003 | Fastovsky et al. |
| 2003/0125793 A1 | 7/2003 | Vesely |
| 2003/0130681 A1 | 7/2003 | Ungs |
| 2003/0144686 A1 | 7/2003 | Martinez et al. |
| 2003/0153943 A1 | 8/2003 | Michael et al. |
| 2003/0153945 A1 | 8/2003 | Patel et al. |
| 2003/0163159 A1 | 8/2003 | Patel et al. |
| 2003/0176888 A1 | 9/2003 | O'Connell |
| 2003/0181922 A1 | 9/2003 | Alferness |
| 2004/0010282 A1 | 1/2004 | Kusleika |
| 2004/0158273 A1 | 8/2004 | Weaver et al. |
| 2004/0186510 A1 | 9/2004 | Weaver |
| 2004/0193209 A1 | 9/2004 | Pavcnik et al. |
| 2004/0230220 A1 | 11/2004 | Osborne et al. |
| 2005/0165441 A1 | 7/2005 | McGuckin, Jr. et al. |
| 2005/0165442 A1 | 7/2005 | Thinnes, Jr. et al. |
| 2005/0251199 A1 | 11/2005 | Osborne et al. |
| 2005/0267512 A1 | 12/2005 | Osborne et al. |
| 2005/0267513 A1 | 12/2005 | Osborne et al. |
| 2005/0267514 A1 | 12/2005 | Osborne et al. |
| 2006/0069406 A1 | 3/2006 | Hendriksen et al. |
| 2006/0100660 A1 | 5/2006 | Osborne et al. |

FOREIGN PATENT DOCUMENTS

| | | |
|---|---|---|
| DE | 3429850 A1 | 2/1986 |
| EP | 0270432 A1 | 6/1988 |
| EP | 0348295 A1 | 12/1989 |
| EP | 0350043 A1 | 1/1990 |
| EP | 0430848 A1 | 6/1991 |
| EP | 0437121 A2 | 7/1991 |
| EP | 0462008 A1 | 12/1991 |
| EP | 0472334 A1 | 2/1992 |
| EP | 0701800 A1 | 3/1996 |
| FR | 2587901 | 4/1987 |
| FR | 2649884 | 1/1991 |
| FR | 2672487 | 8/1992 |
| GB | 2200848 A | 8/1988 |
| GB | 2200848 B | 8/1988 |
| SU | 835447 | 6/1981 |
| SU | 1103868 A | 7/1984 |
| SU | 955912 A | 2/1988 |
| WO | WO 91/04716 | 4/1991 |
| WO | WO 91/11972 | 8/1991 |
| WO | WO 95/08567 | 3/1995 |
| WO | WO 95/27448 | 10/1995 |
| WO | WO 96/17634 | 6/1996 |
| WO | WO 01/06952 A1 | 2/2001 |
| WO | WO 03/011188 A1 | 2/2003 |
| WO | WO 2004/049973 A1 | 6/2004 |
| WO | WO 2005/072645 A1 | 8/2005 |
| WO | WO 2005/102210 A1 | 11/2005 |
| WO | WO 2005/102211 A1 | 11/2005 |
| WO | WO 2005/102212 A1 | 11/2005 |
| WO | WO 2005/102213 A1 | 11/2005 |
| WO | WO 2005/102214 A1 | 11/2005 |
| WO | WO 2006/036867 A1 | 4/2006 |

OTHER PUBLICATIONS

International Search Report—PCT/US2005/013160) Sep. 22, 2005).
International Search Report—PCT/US2005/013281 (Oct. 7, 2005).
International Search Report—PCT/US2005/013322 (Sep. 23, 2005).
International Search Report—PCT/US2005/013323 (Sep. 23, 2005).
International Search Report—PCT/US2005/034350 (Feb. 10, 2006).
International Preliminary Report on Patentability; PCT/US2005/040299;(Nov. 4, 2007).
J.L. Kraimps et al., Annals of Vascular Surgery, Mar. 1992, 99-110.
James Hansen, Metal That Remember, 44-47.
Jean-Louis Kraimps, M.D. et al., Optimal Central Trapping (OPCETRA) Vena Cava Filter: Results of Experimental Studies, Nov. 1992, 697-699.
Morris Simon et al., Transvenous Devices for the Management of Pulmonary Embolism, 1980, 112-121.
Morris Simon, M.D. et al., A Vena Cava Filter Using Thermal Shape Memory Alloy, Oct. 1977, 89-94.

* cited by examiner

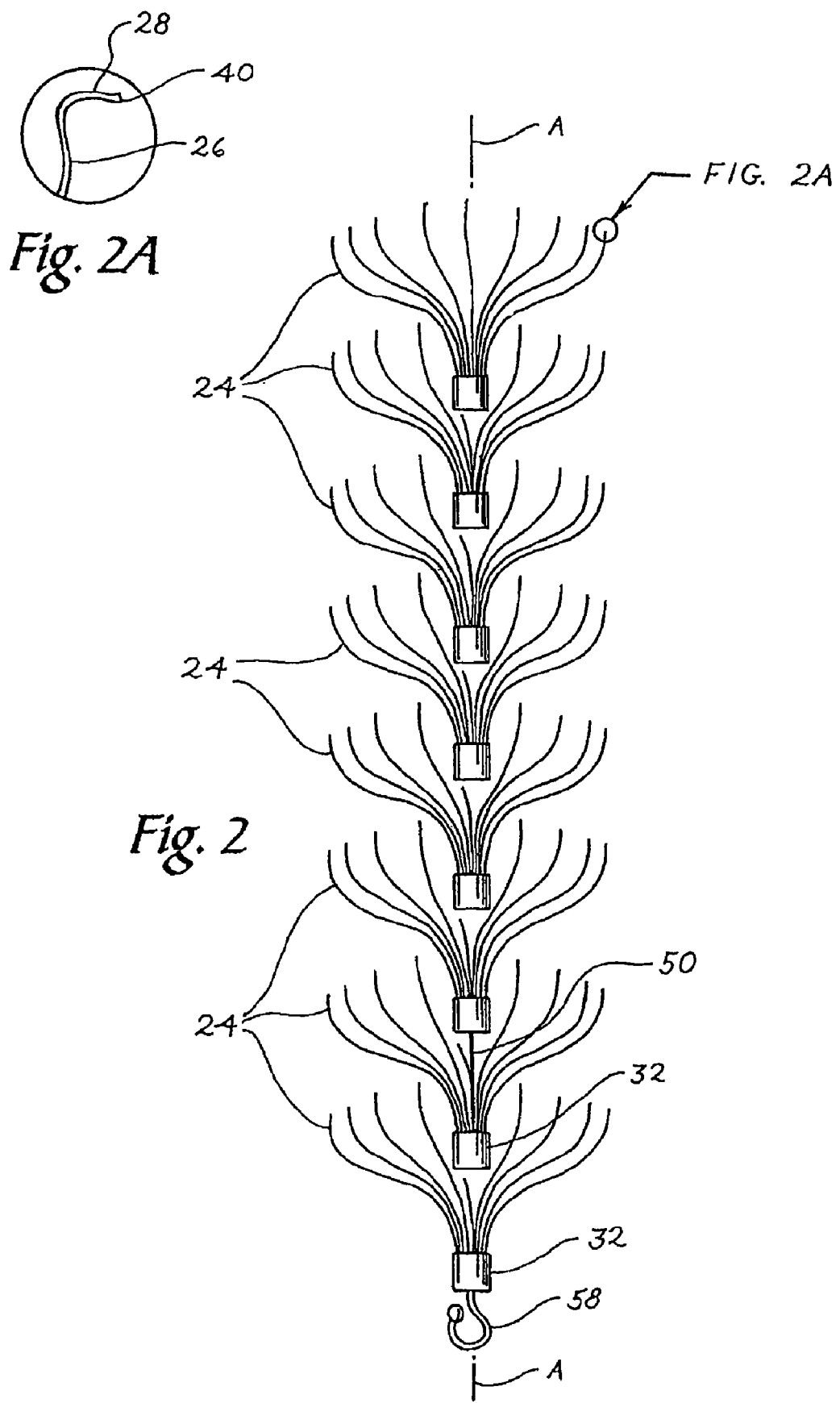

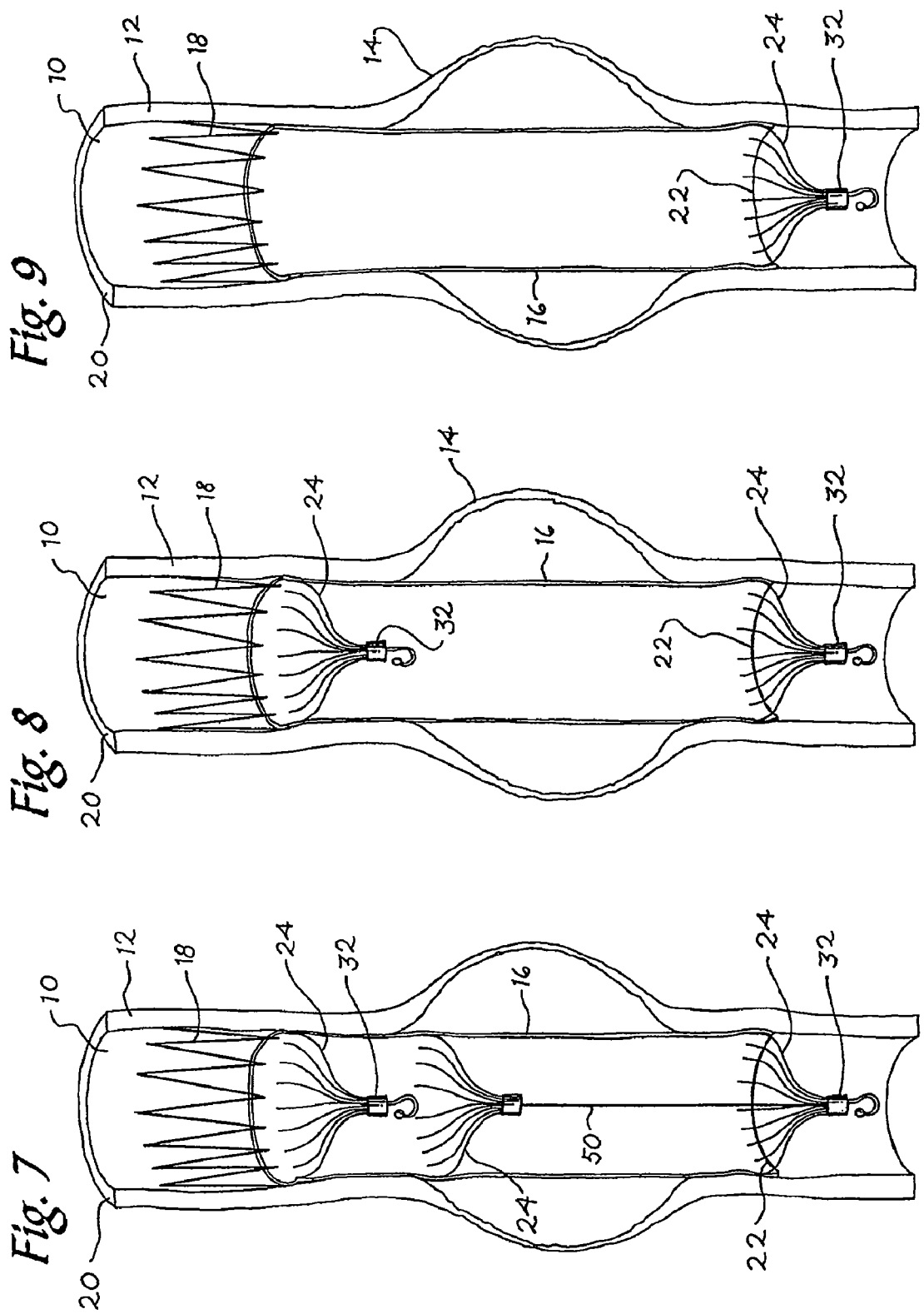

ENDOVASCULAR GRAFT WITH SEPARATELY POSITIONABLE AND REMOVABLE FRAME UNITS

RELATED APPLICATIONS

This application claims the benefit of priority from U.S. Provisional Application No. 61/017,051 filed Dec. 27, 2007, which is incorporated herein by reference.

TECHNICAL FIELD

This invention relates to medical devices. In particular, this invention relates to customizable endoluminal devices having separate frame units, also known as stent units, which may be individually inserted, placed, repositioned and/or removed from a tubular graft within a body vessel. This application also provides an apparatus and method for delivery, placement, and removal of the removable frame units.

BACKGROUND

The functional vessels of human and animal bodies, such as blood vessels and ducts, occasionally weaken or even rupture. For example, in the aortic artery, the vascular wall can weaken or tear, resulting in dangerous conditions such as aneurysms and dissections. Upon further exposure to hemodynamic forces, such an aneurysm can rupture.

One intervention for weakened, aneurismal, dissected or ruptured vessels is the use of an endoluminal device or prosthesis such as a stent graft to provide some or all of the functionality of the original, healthy vessel and/or preserve any remaining vascular integrity by replacing a length of the existing vessel wall that contains the site of vessel weakness or failure. Stent grafts can effectively exclude the aneurysm by sealing both proximally and distally to the aneurysm, and shunting blood through its length. A device of this type can, for example, treat various arterial aneurysms, including those in the thoracic aorta, abdominal aorta, iliac, or hypogastric artery.

Conventional stent grafts are generally formed from a tube of biocompatible material in combination with one or more stents permanently attached to the graft prior to insertion into the body to maintain a lumen therethrough. In some cases, the stents are individual rings placed along the length of the graft and either connected to one another by some means, such as struts, sutures and the like, or are affixed to the graft material by means such as suturing to, gluing to, weaving through, or encasing in the graft material. Other stents are single body stents such as laser cut tubes, mesh or braided tubes, helically coiled tubes, and the like.

In all of these instances, the stents are substantially permanently attached to the graft material and remain attached to the graft material after placement in the vessel. Hence, once the stent graft is placed in the vessel, the stents cannot be repositioned within the graft or removed from the graft, unless the entire device is surgically removed.

In addition, in many instances, the graft material that contacts the vessel wall over time becomes part of the vessel wall, such as in the case of aneurysm repair, and hence, replaces the native vessel. In this case, many of the stents in the stent graft may no longer be needed. And, over time, the stents may break and wear through the graft material, necessitating repair of the graft, and forcing the patient to endure yet another procedure.

Further, many current stent grafts are limited in their ability to accommodate a tortuous native vessel, the shape of which may change over time. Stent grafts may need to be more flexible in certain areas than in others. However, once placed, there is little or no ability to adjust the stent graft in situ to accommodate tortuosity or changes in vessel configuration.

Thus, there remains a need for a customizable stent graft that can accommodate individual anatomies and can be reconfigured in situ and/or removed from the body as needed.

SUMMARY

This invention relates to medical devices. In particular, this invention relates to customizable endoluminal devices having separate frame units that may be individually inserted, placed, repositioned and/or removed from a tubular graft within a body vessel. This application also provides an apparatus and method for delivery and placement of the removable frame units.

Specifically, the device for repairing a vessel of the body includes a tubular graft having a proximal end, a distal end, and a lumen therethrough. The graft has a collapsed configuration for delivery into the vessel and an expanded configuration for at least partially engaging the vessel. The graft is made out of biocompatible material that is capable of incorporation into the vessel wall to permanently engage the vessel wall. A plurality of distinct and independently insertable, positionable, and expandable frame units are removably disposed within the lumen of the tubular graft, with each having an expanded configuration and a collapsed configuration, where each frame unit is comprised of a plurality of expandable members, where at least a portion of the expandable members, when in the expanded configuration, contacts a distinct portion of an inner surface of the tubular graft to expand that portion of the graft, and where each frame unit is configured to be collapsed and repositioned within the tubular graft or removed from the tubular graft.

The number and orientation of frame units within the graft may vary and is application dependent. It is this ease of configurability that allows for the frame units to be placed in an orientation to allow the tubular graft to conform to accommodate for the tortuosity or changes in vessel configuration. In addition, the frame units may be repositioned or removed to optimize the incorporation of the tubular graft into the vessel wall. The removability of each frame unit minimizes the chances that the stent will break and/or wear through the graft material, necessitating repair of the graft, and forcing the patient to endure yet another procedure.

In another example, a device for repairing a vessel of a body includes a tubular graft having a proximal end, a distal end, and a lumen therethrough, where the graft has a collapsed configuration for delivery into the vessel and an expanded configuration for at least partially engaging the vessel. The graft further comprises a biocompatible material capable of incorporation into the vessel wall to permanently engage the vessel wall. A plurality of distinct and independently positionable, expandable frame units, capable of being independently inserted, positioned, repositioned, or removed to conform the tubular graft to the anatomy of the vessel wall, are disposed within the lumen of the tubular graft, each having an expanded configuration and a collapsed configuration.

In one example, each frame unit comprises a hub defined by a longitudinal axis, and a plurality of expandable members extending from the hub, having a first end and a second end, each member having a collapsed configuration for insertion into the vessel and for subsequent removal from the vessel and an expanded configuration where at least a portion of the expandable members contacts a distinct portion of an inner surface of the tubular graft to expand that portion of the graft.

Each frame unit is configured to be collapsed and repositioned within the tubular graft or removed from the tubular graft entirely.

In yet another example, a method for repairing a vessel of a body includes inserting a graft in the location of the vessel to be repaired, securing the graft in the location of the vessel to be repaired, inserting a plurality of distinct and independently positionable, expandable frame units in an unexpanded position, positioning the frame unit within the tubular graft to conform to the anatomy of the vessel, and expanding the frame unit such that at least a portion of the frame unit radially expands a radial force against the lumen of the tubular graft.

The plurality of independently positionable, expandable frame units may also be positioned within a tubular graft that is placed within a curved vessel. The frame units may vary in size and location to accommodate for the non-uniformity of the vessel geometry. This is one feature which allows for placement of the tubular graft in locations within the vessel where conventional stent grafts are unable to be placed.

These and other advantages, as well as the invention itself, will become apparent in the details of construction and operation as more fully described below. Moreover, it should be appreciated that several aspects of the invention can be used with other types of implantable medical devices for the treatment of aneurysms.

BRIEF DESCRIPTION OF THE DRAWINGS

FIG. 2 shows the plurality of frame units outside of the graft.

FIG. 3b is a top view of the configuration shown in FIG. 3a.

FIG. 7 shows a graft having three individual repositionable and removable frame units spaced within the graft.

FIG. 8 shows a graft having two individual repositionable and removable frame units spaced within the graft.

FIG. 9 shows a stent graft having a permanently placed stent at one end and a repositionable and removable frame unit at the other end.

DETAILED DESCRIPTION OF THE INVENTION

To help understand this invention, the following definitions are provided with reference to terms used in this application.

Throughout this specification and in the appended claims, when discussing the application of this invention with respect to the aorta or other blood vessels, the term "distal" with respect to such a device is intended to refer to a location that is, or a portion of the device that when implanted, is further downstream with respect to blood flow; the term "distally" means in the direction of blood flow or further downstream. The term "proximal" is intended to refer to a location that is, or a portion of the device that when implanted is, further upstream with respect to blood flow; the term "proximally" means in the direction opposite to the direction of blood flow or further upstream.

The term "prosthesis" means any replacement for a body part or function of that body part. It can also mean a device that enhances or adds functionality to a physiological system.

The term "endoluminal" describes objects that are found or can be placed inside a lumen in the human or animal body. A lumen can be an existing lumen or a lumen created by surgical intervention. This includes lumens such as blood vessels, parts of the gastrointestinal tract, ducts such as bile ducts, parts of the respiratory system, etcetera. "Endoluminal prosthesis" is thus a prosthesis that can be placed inside one of these lumens. A graft with removable frames is a type of endoluminal prosthesis.

This invention relates to customizable endoluminal devices having separate frame units that may be individually inserted, placed, repositioned and/or removed from a tubular graft within a body vessel. This application also provides an apparatus and method for delivery and placement of the removable frame units.

Figure 1:
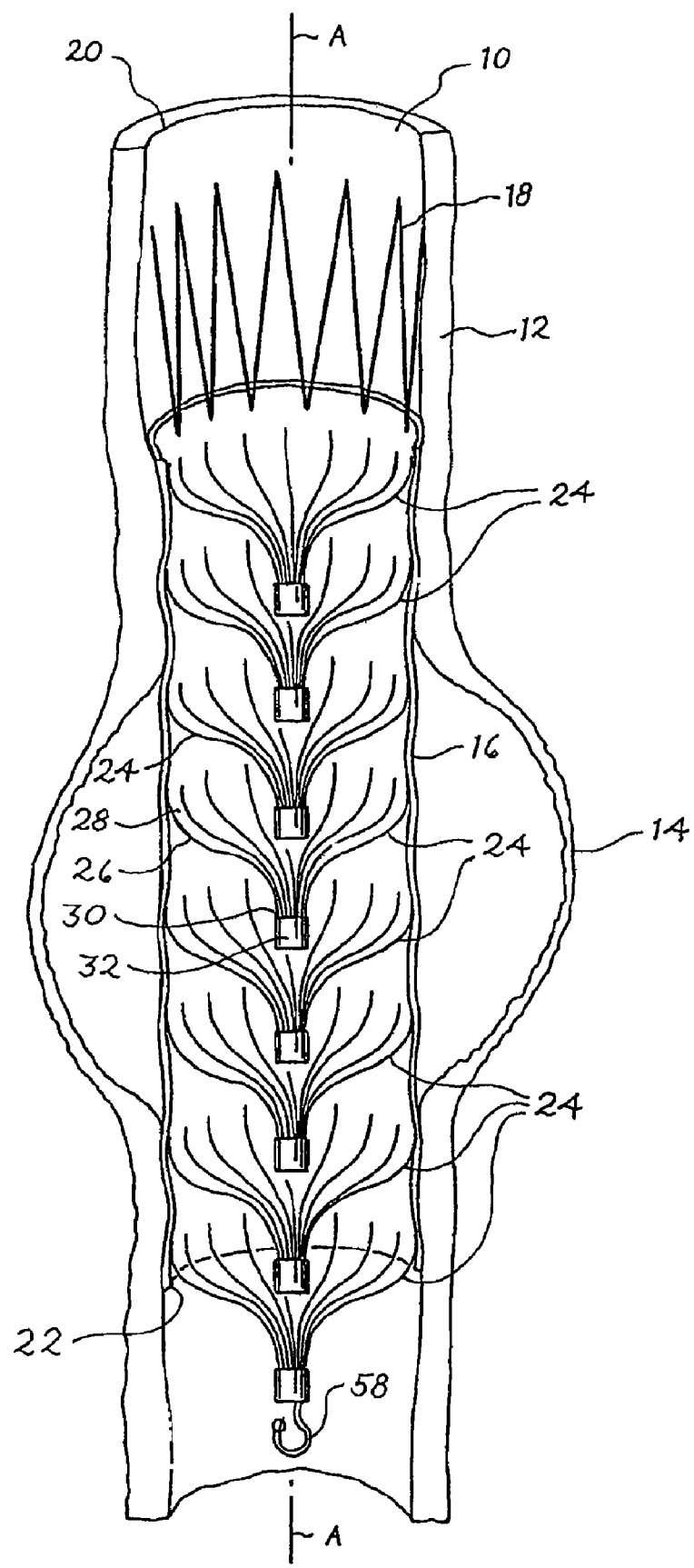
FIG. 1 shows a graft having a plurality of individual frame units deployed within a vessel and spanning an aneurismal region.

FIG. 1 shows a prosthesis 10 as described below, implanted in a body vessel 12, such as an aorta. As shown, the body vessel 12 has an aneurysm 14. As shown, the prosthesis 10, has a proximal end 20 and a distal end 22, with a tubular graft 16 disposed therethrough. The prosthesis 10 also includes an external expandable zig-zag frame unit 18 disposed at the proximal end 20, which is used to affix the graft 16 within the body vessel 12. The zig-zag frame unit 18 may comprise a stent extending from the proximal end 12 and may be of any form so long as it functions to assist in the attachment of the prosthesis 10 to the wall of the body vessel 12. For example, the frame unit 18 may be balloon expandable or self-expandable.

Within the graft 16, a number of frame units 24 have been placed. Each unit 24 may be separately and individually placed independent of the other units 24. The units 24 may also be independently positioned or repositioned within the prosthesis 10, and may be independently removed from the prosthesis 10.

Figure 3A:
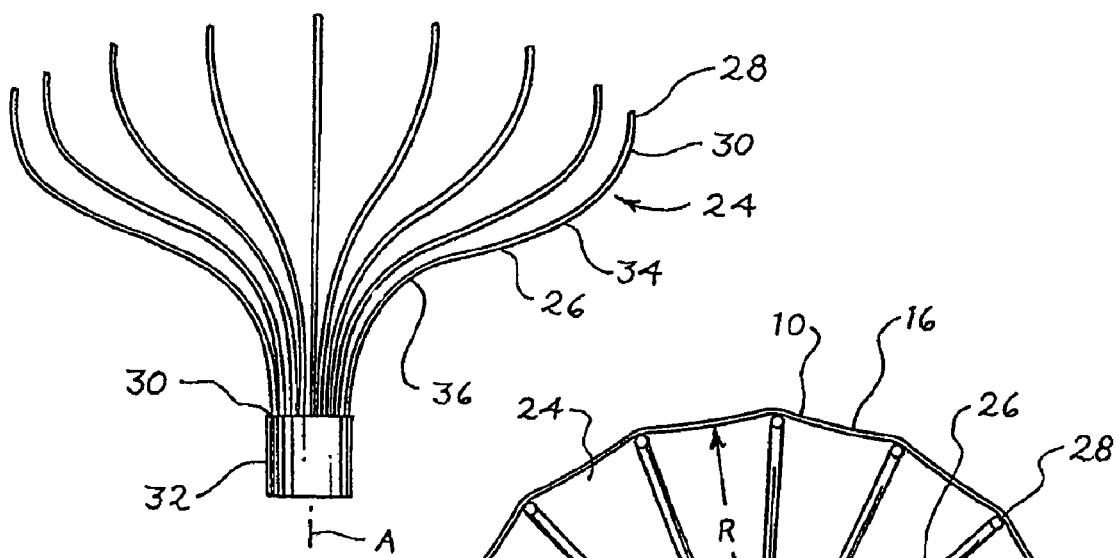
FIG. 3a shows one configuration of a positionable and removable frame unit.

FIG. 2 shows a plurality of frame units 24 outside of the tubular graft 16. As shown in FIG. 3A, each frame unit 24 may be comprised of a plurality of members 26 having a proximal end 28 and a distal end 30, where at least a portion of the members 26 expand outwardly from a longitudinal axis A of the prosthesis 10. The proximal ends 28 of the members 26 may, for example, expand outwardly away from the longitudinal axis A while the distal ends 30 converge toward the axis A. The distal ends 30 may be secured by a cap 32. The cap 32 may hold the distal ends 30 of the members 26 in place by crimping, soldering, or tying the distal ends 30 together. The diameter of the cap 32 may be equivalent to, or slightly larger than, the cumulative diameter of the members 26 included in the frame unit 24. The cap 32 may be provided with a snaring member 58, which may comprise of an eyelet, hook, loop, or a combination thereof, to facilitate removal or repositioning of the frame unit 24. Alternatively, the cap 32 may be magnetically attracted to snaring member 58.

The members 26 of the frame units 24 may be constructed of any suitable material that may be self-expandable, balloon-expandable, or a combination thereof. For example, the members 26 of the frame units 24 may be made out of a superelastic material, stainless steel wire, Nitinol, cobalt-chromium-nickel-molybdenum-iron alloy, cobalt chrome-alloy, or any other suitable material that will result in a balloon-expandable, self-opening, or self-expanding frame unit 24. The frame units 24 also may be constructed of a material that is plastically expandable.

The frame units 24 may be MRI compatible to permit viewing of the prosthesis 10 and each stent 24 with magnetic resonance imaging. The frame unit 24 may be comprised of a metal or metal alloy that provides MRI compatibility. In particular, the implantable medical devices may include titanium metal alloys, molybdenum metal alloys and palladium metal alloys having low magnetic susceptibility and increased radiopacity while maintaining MRI compatibility.

Furthermore, the members 26 of the frame units 24 may be formed from wire having a round cross-section with a diameter of at least about 0.010 inches to about 0.050 inches. Of course, it is not necessary that the members 26 have a round or near-round cross-section. For example, the members 26 could take on any shape with rounded edges so long as a non-turbulent flow is maintained through the graft 16.

As shown in FIG. 3A, the members 26 may have an arcuate segment 34 having a gradual S-shape. Each arcuate segment 34 may have a first curved portion 36 that is configured to gradually bend away from a longitudinal or central axis A of the frame unit 24 and a second curved portion 38 that is configured to gradually to bend toward the longitudinal axis A of the frame unit 24. In one example, each arcuate segment 34 has a thickness of at least about 0.018 inch and a tensile strength of between about 200,000 pounds per square inch ("psi") and 400,000 psi.

In one example, shown in FIG. 2, the proximal ends of the members 26 may include optional anchoring hooks 40 to anchor the frame unit 24 in the prosthesis 10 when the frame unit 24 is deployed at the desired delivery location within the body vessel 12 or other blood vessels. Each anchoring hook 40 is integral with the arcuate segment 34 and can have the thickness and the tensile strength of the arcuate segment 34. It can be appreciated that the members 26 may not have uniform thickness or tensile strength within each member 26 or with respect to one another within the same unit 24. The members 26 are configured to move between an expanded state for engaging the anchoring hooks 40 with the tubular graft 16 and an unexpanded state or configuration for retrieval, repositioning, or delivery.

Figure 3B:
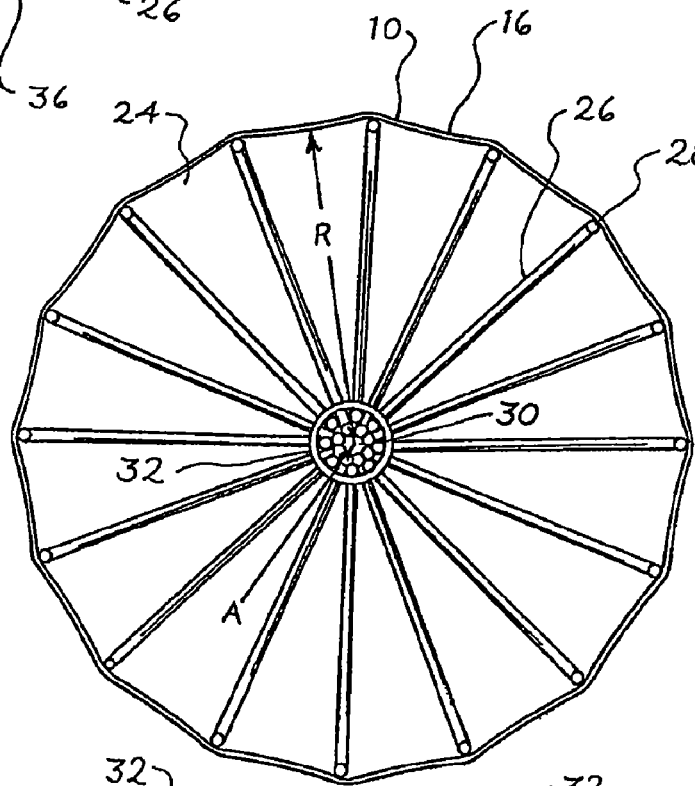

In the expanded state, as shown in FIG. 1, each arcuate segment 34 extends arcuately along a longitudinal axis A, as shown in FIG. 3A, and linearly relative to radial axis R, as shown in FIG. 3B, from the distal end 30 of the member 26 to the proximal end 28 of the member 26. As shown in FIG. 3B, the members 26 radially extend from the distal ends 30, defining the radial axis R. In this example, the members 26 extend linearly relative to the radial axis R and avoid entanglement with other members 26. In this example, each frame unit 24 includes 16 members 26 spaced radially about the longitudinal axis A of the frame unit 24. It can be appreciated that the number of members 26 may vary within each frame unit 24, and may or may not be equally spaced apart from one another. Moreover, it is not necessary that the members 26 all have the same length and/or diameter. The members 26 extend from the cap 32 and radially expand out from the longitudinal axis A.

The anchoring hooks 40 engage the walls of the tubular graft 16 to define a first axial portion to secure the frame unit 24. The anchoring hooks 40 prevent the frame unit 24 from migrating from the delivery location in the blood vessel 12 where it is disposed. The members 26 are shaped such that, when the frame unit 24 is freely expanded, the frame unit 24 has a diameter of between about 25 mm and 45 mm and a length of between 3 cm and 7 cm. The members 26 have sufficient spring strength such that the proximal end 28 of the member 26 secures the tubular graft 16 against the vessel wall of the body vessel 12 once the frame unit 24 is deployed.

As shown in FIGS. 1 and 3B, when each frame unit 24 is deployed within the prosthesis 10, the outer surface of at least the proximal ends 28 of the members 26 engage the walls of the tubular graft 16 as to apply sufficient radial force to support the tubular graft 16 in an open configuration, and where at least a portion of the tubular graft 16 contacts the vessel wall 12, to hold the tubular graft 16 in contact with the tissue of the body vessel 12 until the tubular graft 16 has remolded into the vessel tissue or has become incorporated into the vessel wall of the body vessel 12. The frame units 24 may be positioned in any configuration or orientation to conform the graft 10 to the anatomy of the vessel 16.

The tubular graft 16 may consist of any biocompatible material. For example, but without limitation, the graft material 16 may comprise of a film, a coating, a sheet of biocompatible fabric, non-woven materials or porous materials. Examples of biocompatible polymers from which porous sheets can be formed include polyesters, such as poly(ethylene terephthalate), polylactide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethanes ureas, polyurethanes including carbonate linkages and polyurethanes containing siloxane segments. In addition, materials that are not inherently biocompatible may be subjected to surface modifications in order to render the material biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a porous sheet can be used to make a graft material, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes listed above. Preferably the porous sheet is made of one or more polymers that do not require treatment or modification to be biocompatible.

Furthermore, the graft material 16 may be comprised of biocompatible polyurethane. Examples of biocompatible polyurethanes include THORALON® (Thoratec, Pleasanton, Calif.), BIOSPAN®, BIONATE®, ELASTHANE™, PURSIL™ and CARSOSIL™ (Polymer Technology Group, Berkeley, Calif.). As described in U.S. Pat. No. 6,939,377, incorporated herein by reference in its entirety, Thoralon® is a polyetherurethane urea blended with a siloxane-containing surface modifying additive. Specifically, the polymer is a mixture of base polymer BPS-215 and an additive SMA-300. The concentration of additive may be in the range of 0.5% to 5% by weight of the base polymer. The BPS-215 component (Thoratec® Corporation, Pleasanton, Calif.) is a segmented polyether urethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). The SMA-300 component (Thoratec® Corporation, Pleasanton, Calif.) is a polyurethane comprising polydimethylsiloxane as a soft segment and the reaction product of MDI and 1,4-butanediol as a hard segment. A process for synthesizing SMA-300 is described, for example, in U.S. Pat. Nos. 4,861,830 and 4,675,361, which are incorporated herein by reference.

The graft material 16 may also include extracellular matrix materials. The "extracellular matrix" is typically a collagen-rich substance that is found in between cells in animal issue and serves as a structural element in tissues. Such an extracellular matrix is preferably a complex mixture of polysaccharides and proteins secreted by cells. The extracellular matrix can be isolated and treated in a variety of ways. Following isolation and treatment, it is referred to as an "extracellular matrix material," or ECMM. ECMMs may be isolated from submucosa (including small intestine submucosa), stomach submucosa, urinary bladder submucosa, tissue mucosa, renal capsule, dura mater, liver basement membrane, pericardium or other tissues.

Purified tela submucosa, a preferred type of ECMM, has been previously described in U.S. Pat. Nos. 6,206,931, 6,358,284 and 6,666,892 as bio-compatible, non-thrombogenic material that enhances the repair of damaged or diseased host tissues. U.S. Pat. Nos. 6,206,931, 6,358,284 and 6,666,892 are incorporated herein by reference. Purified submucosa extracted from the small intestine ("small intestine submucosa" or "SIS") is a more preferred type of ECMM for use in this invention. Another type of ECMM, isolated from liver basement membrane, is described in U.S. Pat. No. 6,379,710, which is incorporated herein by reference. ECMM may also be isolated from pericardium, as described in U.S. Pat. No. 4,502,159, which is also incorporated herein by reference. These features of the graft material allow for the frame units 24 to be removed after the incorporation of the graft material into the wall of the vessel 12.

Figures 4, 5, 6:
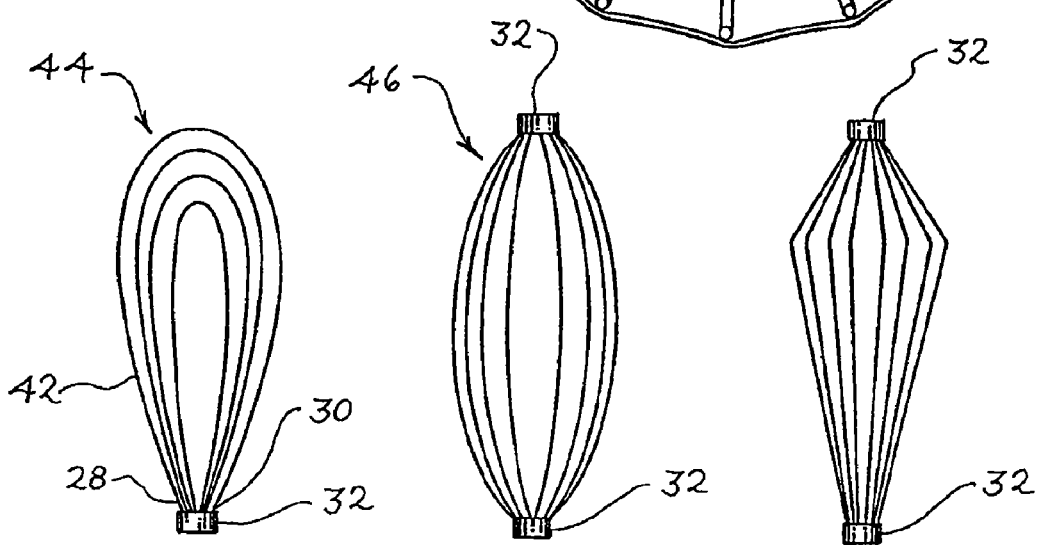
FIG. 4 shows another configuration of a positionable and removable frame unit.
FIG. 5 shows another configuration of a positionable and removable frame unit.
FIG. 6 shows another configuration of a positionable and removable frame unit.
Figure 10:
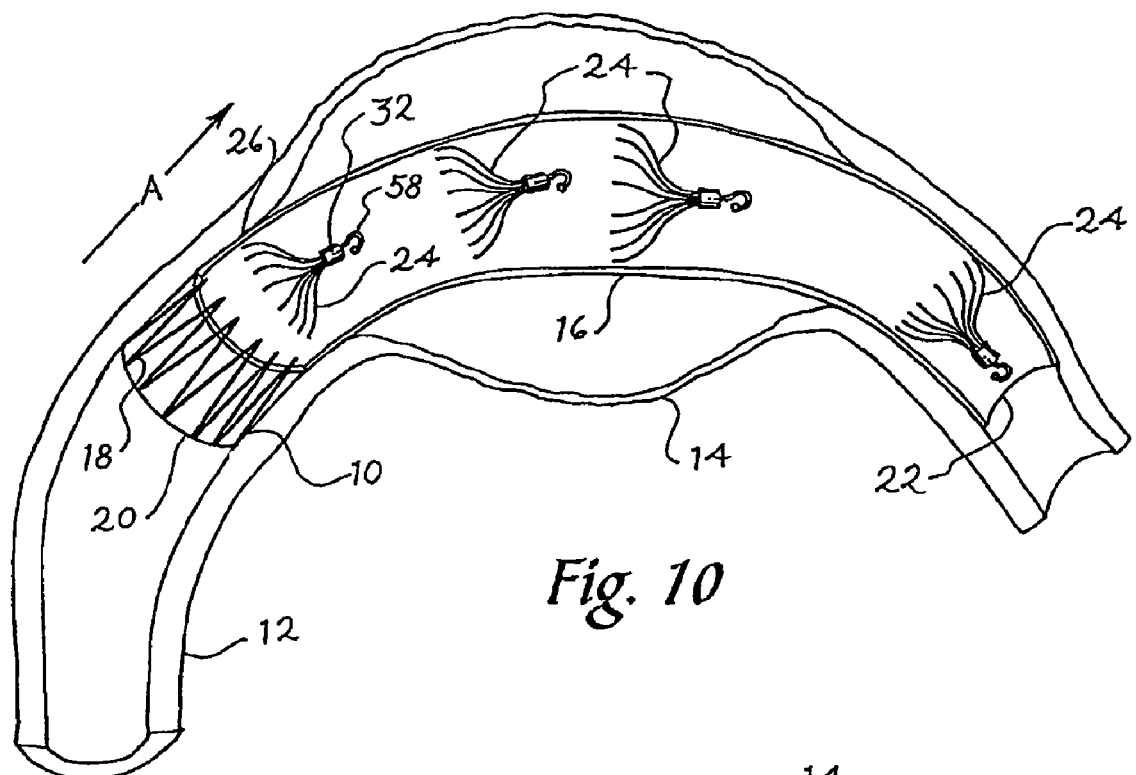
FIG. 10 shows a stent graft having a number of repositionable and removable frame units in a graft accommodating a curved vessel.
Figure 11:
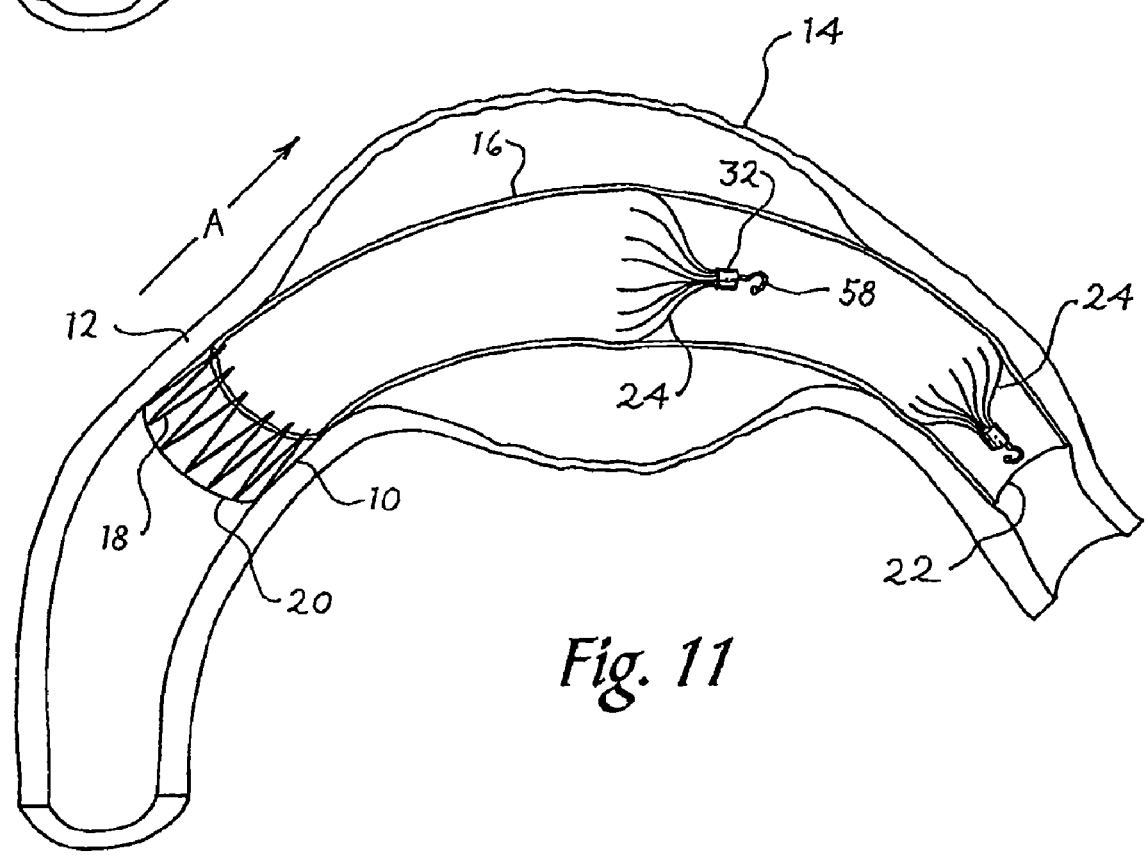
FIG. 11 is another stent graft having a number of repositionable and removable frame units in a graft accommodating a curved vessel.

The configuration of the individual frame unit 24 may also vary, such as those shown in FIGS. 4-6. For example, FIG. 4 shows the frame unit 24 with loop-shaped members 42, where the proximal end 28 and the distal end 30 of each of the loop-shaped members 42 are retained by, or coupled to, the cap 32, forming an enclosed frame unit 44. FIG. 5 shows a parabolic frame unit 46 comprising two caps 32 with a plurality of members 26. The ends of each member 26 are retained by, or coupled to, the two caps 32. The members 26 are continuous and may have a parabolic shape 48, as shown in FIG. 5. The members 26 may also have an arch shape with a vertex 48, as shown in FIG. 6.

Independent of the frame unit 24 configuration, the members 26 will exert a radial force sufficient to allow the tubular graft 16 to at least partially incorporate into the vessel wall of the body vessel 12. The members 26 of the enclosed frame units 44, 46 can be made out of the same type of material of the members 26 of the frame unit 24, as discussed previously As shown in FIGS. 7-11, the frame units 24 may be positioned relative to each other to accommodate a particular vessel's shape. For example, as shown in FIG. 7, the frame units 24 may be uniformly spaced or staggered with varying distances between them in any manner necessitated by the particular situation to suit the particular vessel configuration. As shown in FIG. 7, a frame unit 24 may be placed adjacent to the zig-zag frame unit 18 and prior to the aneurysm 14, another frame unit 24 may be placed at the location of the aneurysm 14, and a last frame unit 24 may be placed at a location after the aneurysm 14. In this configuration, the frame units 24 assist the tubular graft 16 to incorporate into the vessel wall of the body vessel 12, while keeping a least a portion of the tubular graft 16 in an expanded configuration.

The configurations of the frame units 24 may further be varied, as shown in FIG. 8. In FIG. 8, a frame unit 24 may be placed adjacent to the zig-zag frame unit 18 with another frame unit 24 placed after the aneurysm 14. In any of these configurations, each frame unit 24 may be independently removed, replaced, or repositioned. FIG. 9 shows yet another configuration, with a single frame unit 24 placed adjacent to the distal end 22 of the tubular graft 16.

As shown in FIGS. 10-13, the prosthesis 10 and the frame units 24 may be placed in a vessel 12 that is not substantially straight. For example, if the aneurysm 14 is located in an aortic region, the placement of the prosthesis 10 may be in a vessel 16 having a radius of curvature, such as the thoracic aorta.

Figure 12:
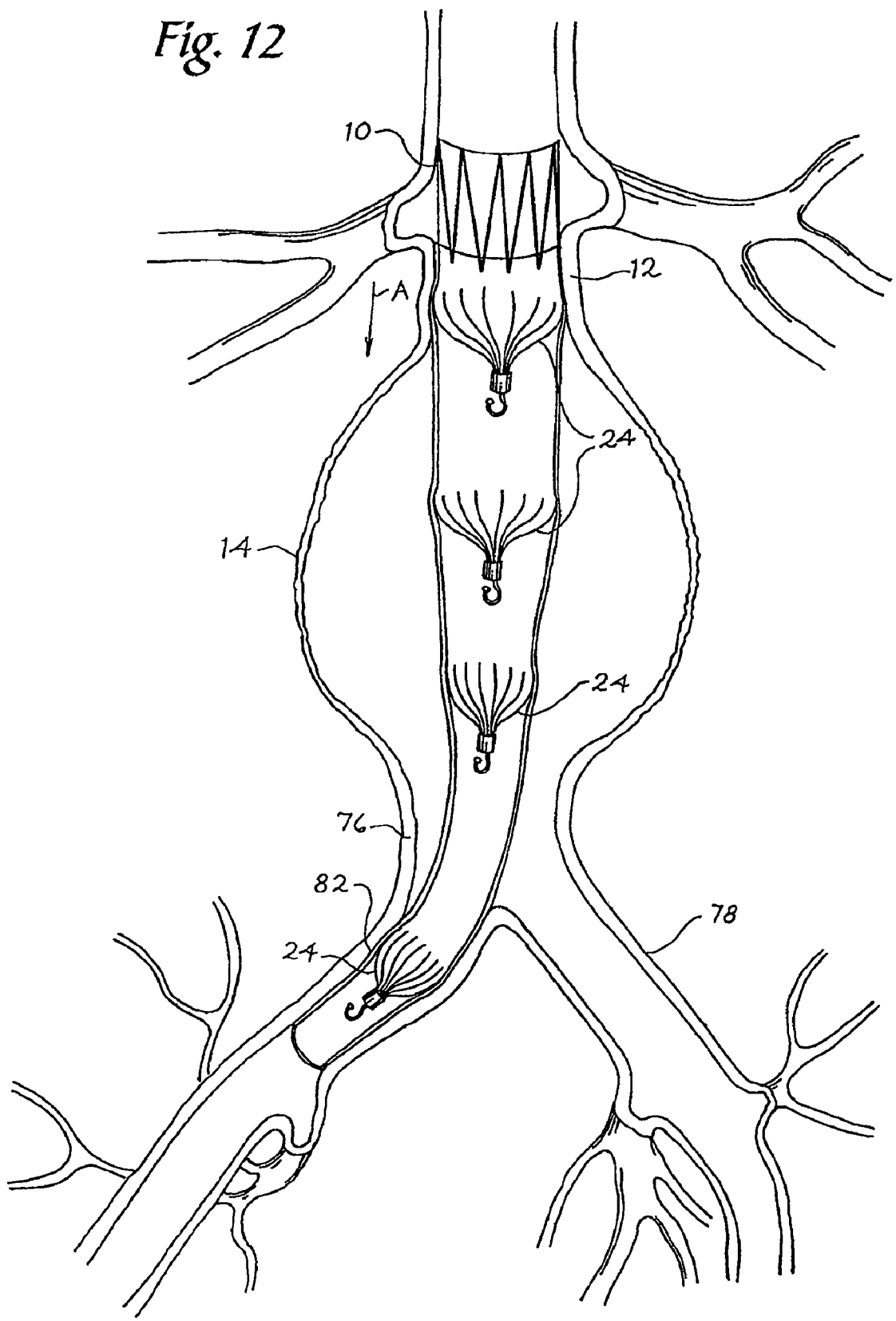
FIG. 12 is another stent graft having a number of repositionable and removable frame units of varying sizes in a graft.
Figure 13:
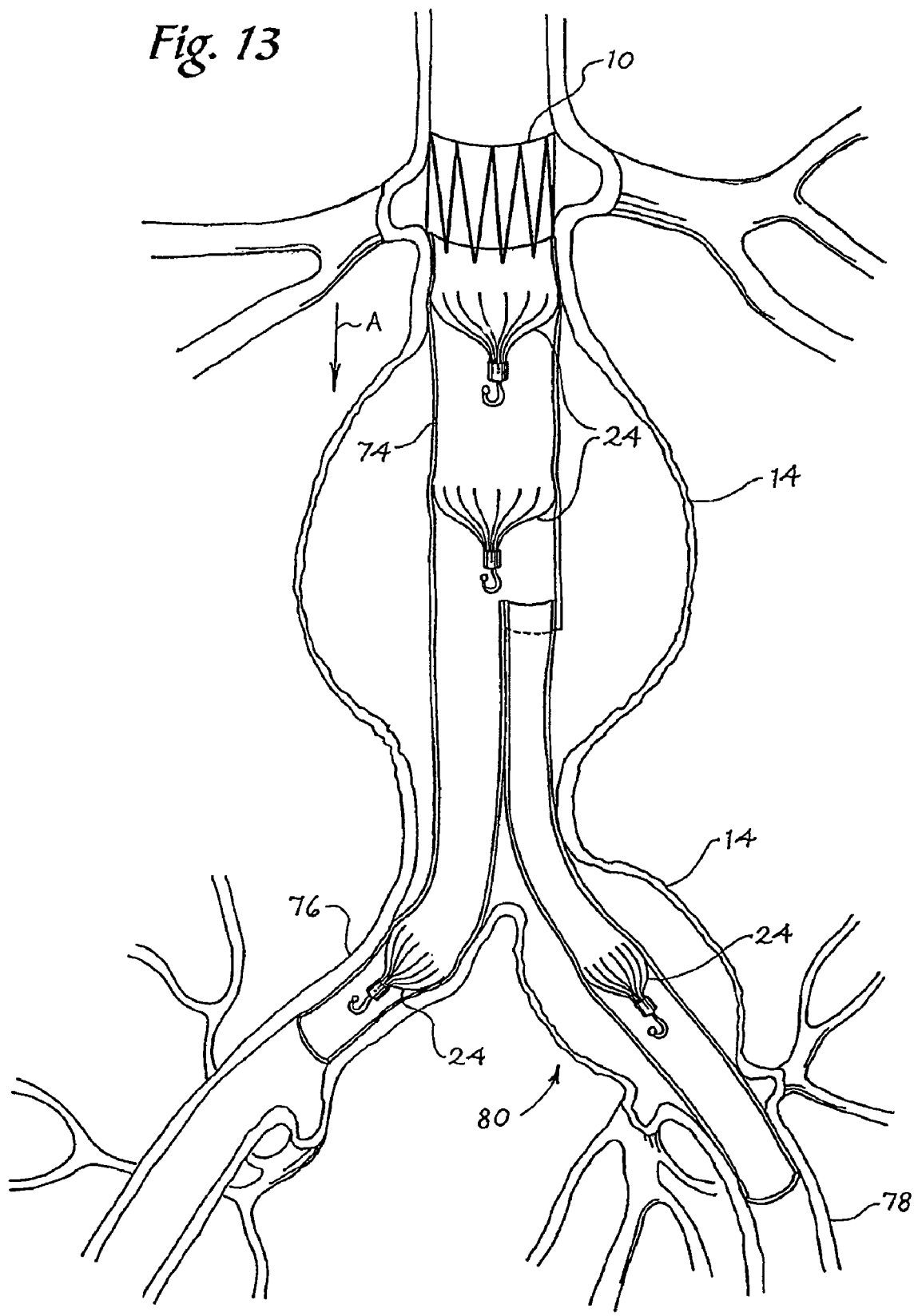
FIG. 13 shows a stent graft having a number of repositionable and removable frame units in a graft accommodating a bifurcated vessel.

As further shown in FIGS. 12 and 13, the size of the frame units 24 may vary to accommodate the varying vessel diameters and may be placed within different types of prosthesis 10, such as a bifurcated graft 74 as shown in FIG. 13. The frame units 24 may be placed in one or both of the ipsilateral 76 or contralateral 78 legs and the body 80. Alternatively, the frame units 24 may also be placed within a tapered graft, such as an aorto-uni graft 82 as shown in FIG. 12.

The direction of the blood flow, as denoted by the arrow A, may dictate the location of the zig-zag frame unit 18 and the direction of the members 26 of the frame units 24. However, it can be appreciated that the zig-zag frame unit 18 may be replaced with a frame unit 24, or may be repositioned anywhere else within the prosthesis 10.

The number of frame units 24 disposed within the prosthesis 10 at any given time may vary from a single unit 24 to a plurality of units 24. Two or more independent frame units 24 may also be coupled together by a connecting member 50, as shown in FIG. 7. For example, a single connecting member 50 may removably connect all of the frame units 24 along the axis of the prosthesis 10 or separate members 50 may connect two adjacent frame units 24. In addition, the number of frame units 24 connected together by the connecting members 50 may vary, and can be rearranged depending on the particular application. The connecting members 50 may be formed from the same type of materials and may have the same shape and size as the members 26 of the frame unit 24. For example, the connecting members 50 may be formed from a superelastic material, stainless steel wire, Nitinol, cobalt-chromium-nickel-molybdenum-iron alloy, or cobalt chrome-alloy, or any other suitable material that will result in a self-opening or self-expanding frame.

Figure 14:
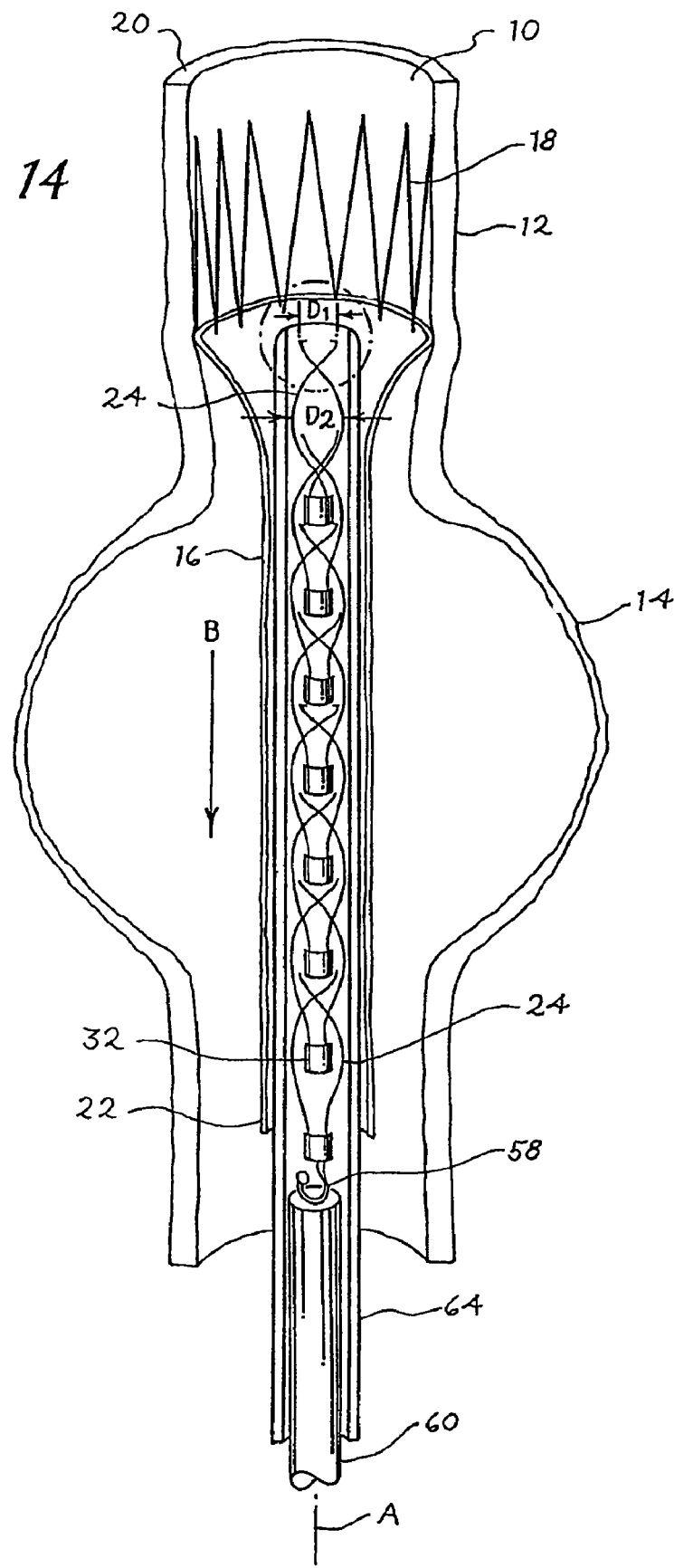
FIG. 14 shows deployment of an endoluminal device including a graft and a plurality of positionable and removable frame units.
Figure 16:
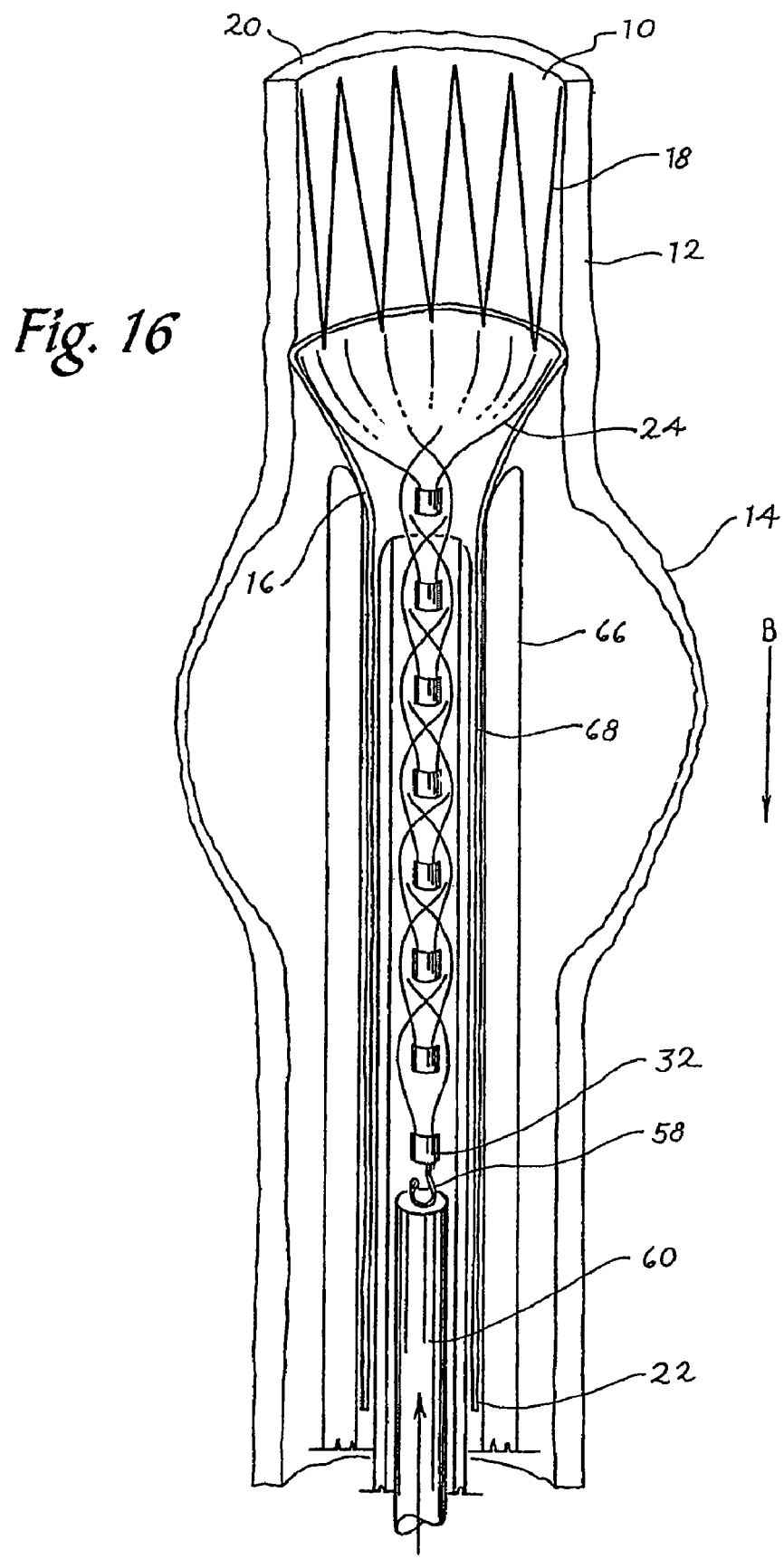
FIG. 16 shows another type of deployment of an endoluminal device including a graft and a plurality of positionable and removable frame units.

FIGS. 14 and 16 illustrate a series of frame units 24 in an unexpanded state disposed in a sheath 64 for delivery. As shown, each frame unit 24 is configured for each member 26 to cross another member 26 along the longitudinal axis A. As a result, in the unexpanded state, the anchoring hooks 40 are configured to invert or inwardly face the longitudinal axis A for simplified retrieval, delivery, or repositioning of the frame unit 24. A concern that the anchoring hooks 40 may scrape, scratch, or tear the inner wall of a sheath is eliminated, since the members 26 of the frame unit 24 are shaped to allow the anchoring hooks 40 to face each other in the unexpanded state.

Because each member 26, when in the unexpanded state, is configured to cross another member 26 along the longitudinal axis A such that the arcuate segments 34, the first curved portions 36, and the second curved portion 38, occupy a first diameter $D_1$, which is between about 6 French (or 0.0792") and 14 French (or 0.1848"), where one French unit is about 0.0132". In this example, the first diameter, $D_1$, is greater than a second diameter $D_2$, of about 3 French (or 0.0396") and 9 French (or 0.1188"), occupied by the anchoring hooks 40 for retrieval or delivery. It can be appreciated that the first diameter, $D_1$, of the arcuate segments 34 allows for the anchoring hooks 40, occupying the second diameter $D_2$, to be removed without scraping, tearing, or displacing the tubular graft 16 or vessel wall of the vessel 12.

An alternative example of the present invention eliminates the anchoring hooks 40 from the proximal ends 28 of the members 26. If no anchoring hooks 40 are present, the radial force of the members 26 are designed to have sufficient spring strength to secure each of the frame units 24 with the tubular graft 16 and vessel wall of the body vessel 12.

Figure 15:
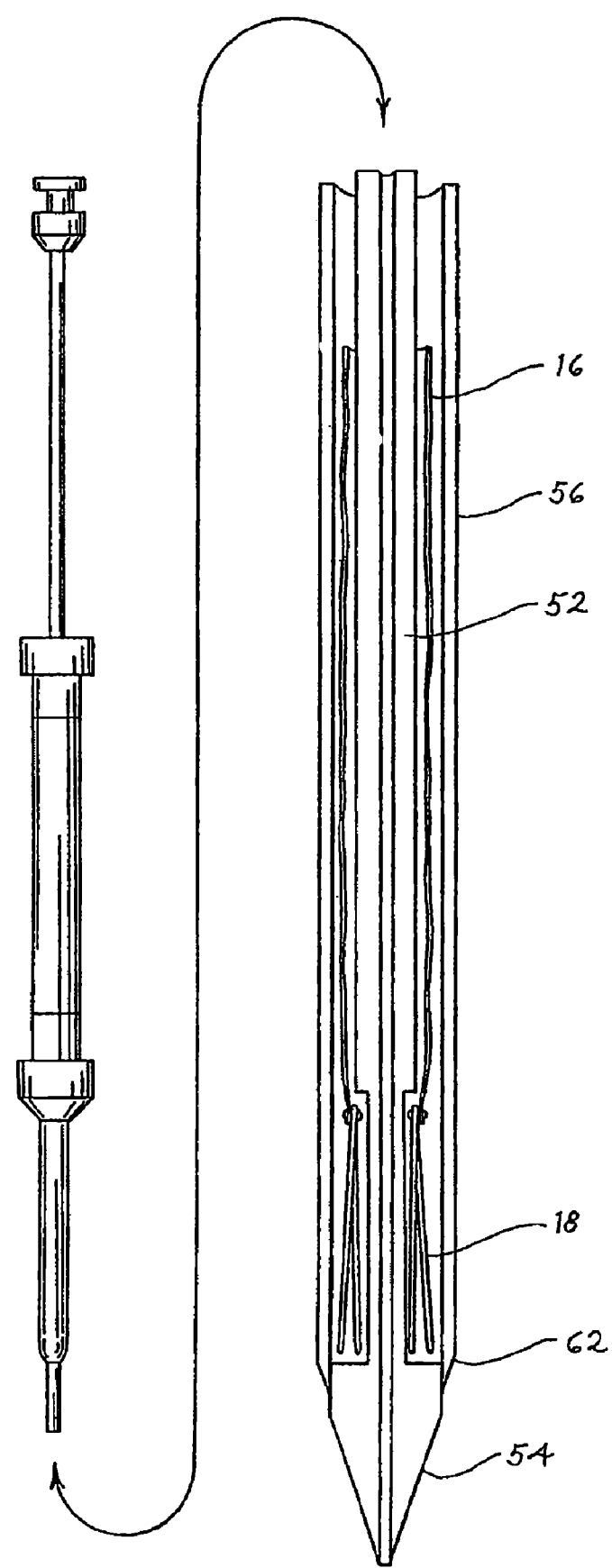
FIG. 15 is an exemplary delivery device.

It can be appreciated that the prosthesis 10 and the frame units 24 may be delivered or repositioned by any suitable introducer. For example, as shown in FIG. 15, the tubular graft 16 may be first inserted and secured with a first dilator 54, followed by the introduction of the frame units 24 with the sheath 64 and second dilator. For removal, the frame units 24 may be removed by any suitable introducer tube (not shown). By way of example, the introducer tube may have an inside diameter of between 4.5 French (or 0.0594") and 16 French (or 0.2112"), and more preferably between about 6.5 French (or 0.0858") and 14 French (or 0.1848"). Thus, the collapsed state of the frame unit 24 may be defined by the inside diameter of the introducer tube.

FIG. 14 illustrates the tubular graft 16 deployed within the body vessel 12, and the frame units 24 within the sheath 56. A pusher 60 is located adjacent to the snaring member 58. In operation, the tubular graft 16 is first deployed within the body vessel 12. For deployment of the tubular graft 16 containing the zig-zag frame unit 18, the sheath 56 and the dilator 54, as shown in FIG. 15, are percutaneously inserted through the patient's vessel such that a proximal end 62 of the sheath 56 is positioned at a desired deployment location. A wire guide (not shown) may be used to guide the sheath 56 and the dilator 54 through the anatomy and into the desired location. After deployment of the tubular graft 16 and removal of the first sheath 56 and dilator 54 in the direction of the arrow B, a second sheath and dilator are introduced to the location of deployment. After removal of the second dilator in the direction of the arrow B, the frame units 24, in a collapsed configuration, are inserted through the distal end of the sheath 64 using a pusher 60 for delivery to the location of deployment via the femoral vein of the patent.

During deployment, the sheath 64 is removed in the direction of the arrow B and each of the frame units 24 radially expands such that the members 24 of each frame unit 24 apply a radial force along the inner diameter of the tubular graft 16 sufficient to unfurl and secure the graft material to the vessel wall of the body vessel 12. After placement of one frame unit 24, the sheath 64 may be repositioned within the tubular graft 16 to allow for the placement of another frame unit 24 within the tubular graft 16.

Alternatively, each frame unit 24 may be individually loaded into the sheath 64 in a unique spatial orientation to provide for a desired spacing configuration when deployed.

As FIG. 16 illustrates, in another example of the present invention, the frame units 24 with the zig zag frame unit 18 and the graft 10 are placed simultaneously within the body vessel 12. The tubular graft 16 is disposed within an outer sheath 66 and the frame units 24 are disposed within an inner coaxial sheath 68. The most proximal frame unit 24 is attached to the graft 10. The outer sheath 66 is first retracted in the direction of the arrow B. Next, the inner sheath 68 is retracted in the direction of the arrow B and the frame units 24 will deploy inside the graft 10. It can be appreciated that the inner sheath 68 may be retracted prior to the outer sheath 66, and it then would be the retraction of the outer sheath 66 that would allow for the tubular graft 16 to unfurl and for the frame units 24 to expand. Once the inner sheath 62 is retracted, the frame units 24 will be in a partially expanded state inside the graft 10. Once the outer sheath 60 is retracted, the frame units 24 will fully expand as the graft 10 is un-sheathed. It can be appreciated that the inner sheath 68 may be repositioned prior to deploying another frame unit 24 within the tubular graft 16.

Figure 17:
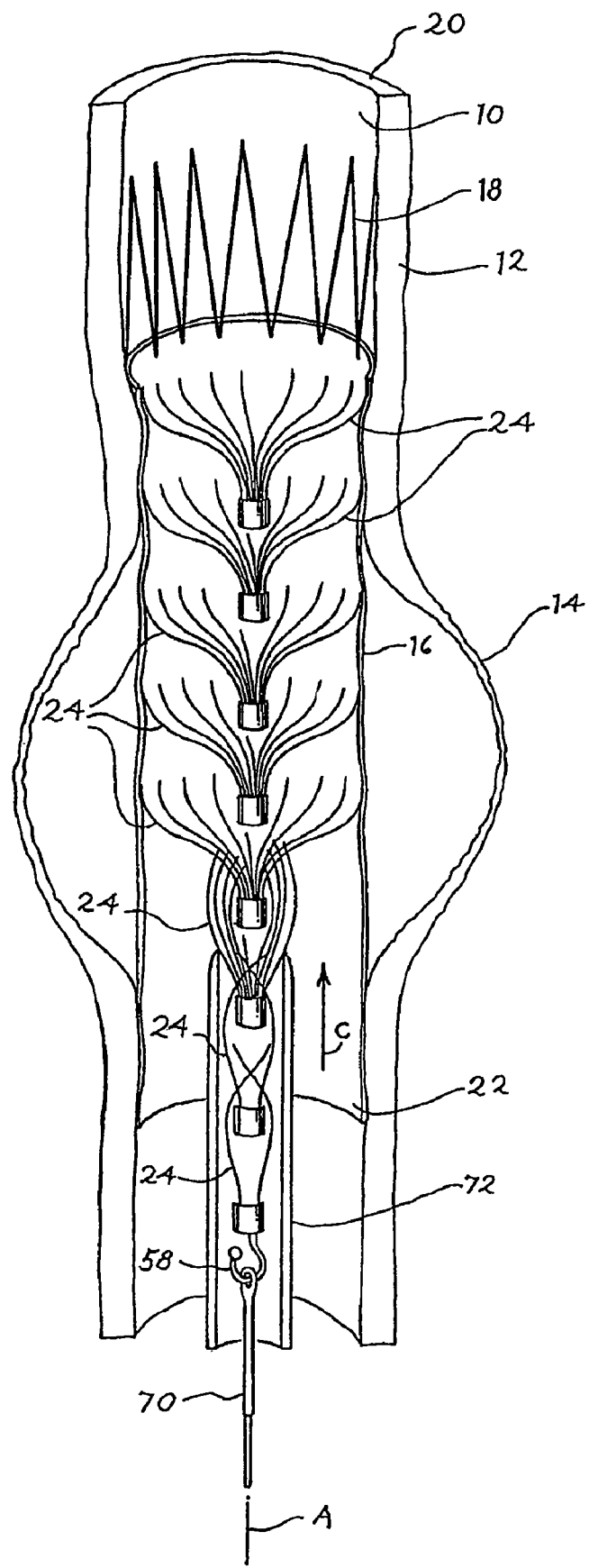
FIG. 17 shows removal or repositioning of the frame units of the stent graft shown in FIG. 16.

FIG. 17 illustrates one example of how to retrieve one or more of the frame units 24 from the tubular graft 16. In operation, a sheath 72 is progressed over the frame unit 24 such that the members 26 converge from a first position, shown in FIG. 1, to a second position, shown in FIG. 16, along the longitudinal axis A. One method to collapse the members 26 into the second position requires holding the frame unit 24 with the snaring device 70, while simultaneously moving the sheath 72 in the direction indicated by the arrow C. Once the frame unit 24 is encapsulated by the sheath 72, and in the second position, the snaring device 70 can retract the frame unit 24 from the tubular graft 16 and the patient. This process may be repeated until the desired number of frame units 24 are removed.

Alternatively, to reposition the frame unit 24 within the tubular graft 16, the same steps as the removal of the frame unit 24 are taken, except that instead of removing the frame unit 24 entirely from the patent, the frame unit 24, once encapsulated within the sheath 72, is repositioned with the sheath 72 along the longitudinal axis A, within the tubular graft 16. Once the frame unit 24 is in the desired position, the sheath 72 is withdrawn in a direction opposite to the arrow C as shown in FIG. 17, and the frame unit 24 is expanded.

It is also contemplated that each individual frame unit 24 may be independently removed from the tubular graft 16. For example, it may be desirable to remove the distal-most frame unit 24. Alternatively, it may be desirable to reposition the frame units 24 within the tubular graft 16. In either scenario, the snaring device 70 may be used to move each frame unit 24. If two or more frame units 24 are coupled together by the connecting member 50, it may be sufficient for the snaring device 70 to retrieve the distal-most frame unit 24 coupled with the connecting member 50, which will in turn cause the retrieval of the adjacent frame units 24 which are also coupled together.

One method for repairing the vessel 12 includes inserting and securing the tubular graft 16 in the location of the vessel 12 to be repaired. One way to secure the graft 16 would be by sowing the graft 16 to the vessel wall 12. A plurality of unexpanded frame units 24 may then be positioned within the graft 16, where each frame unit 24 is positioned within the graft 16 to conform to the anatomy of the vessel 12. Alternatively, the frame units 24 may be simultaneously inserted along with the graft 16. In either event, each frame unit 24 is then expanded such that at least a portion of the frame unit 24 contacts the graft 16 and exerts a radial force against the graft 16. Each frame unit 24 may be collapsed and repositioned, as explained above.

While the present invention has been described in terms of preferred examples, and it will be understood that the invention is not limited thereto since modifications may be made to those skilled in the art, particularly in light of the foregoing teachings.

What I claim is:

1. A device for repairing a vessel of a body, comprising:
   a tubular graft having a proximal end, a distal end, and a lumen therethrough, the graft having a collapsed configuration for delivery into the vessel and an expanded configuration for at least partially engaging the vessel, where the graft comprises a biocompatible material capable of incorporation into the vessel wall;
   a plurality of distinct and independently insertable, positionable, and expandable frame units removably disposed within the lumen of the tubular graft, each frame unit having an expanded configuration and a collapsed configuration, a proximal end and a distal end,
   where each frame unit extends from a hub defined by a longitudinal axis and comprises a plurality of expandable members, and at least a portion of the expandable members in the expanded configuration contacts a distinct portion of an inner surface of the tubular graft to expand that portion of the graft and wherein at least one of the plurality of expandable members has a convex curve towards the longitudinal axis followed by a concave curve away from the longitudinal axis; and
   where each frame unit is collapsible and repositionable within the tubular graft or collapsible and removable from the tubular graft.

2. The device for repairing the vessel of the body in claim 1, where two or more of the frame units are removably coupled together by a connecting member.

3. The device for repairing the vessel of the body of claim 1, where at least one of the plurality of expandable members comprises a hook at a free end of the at least one member.

4. The device for repairing the vessel of the body of claim 1, where each of the plurality of expandable members has a diameter in the range of about 0.010 inches to about 0.050 inches.

5. The device for repairing the vessel of the body of claim 1, further comprising:
   at least one member connecting two or more frame units and
   at least one permanent stent disposed within the tubular graft.

6. The device of repairing the vessel of the body of claim 1, where each frame unit further comprises a capture mechanism at the distal end configured to engage a device for removing the frame unit from the graft.

7. A device for repairing a vessel of a body, comprising:
   a tubular graft having a proximal end, a distal end, and a lumen therethrough, a collapsed configuration for delivery into the vessel and an expanded configuration for at least partially engaging the vessel,
   where the graft comprises a biocompatible material capable of incorporation into the vessel wall to permanently engage the vessel wall;
   a plurality of distinct and independently insertable, positionable, and expandable frame units capable of being independently positioned in, repositioned within, or removed from the tubular graft,
   where each frame unit comprises,
   an expanded configuration and a collapsed configuration;
   a distal end;
   a hub at the distal end; and
   a plurality of expandable members having a first end secured by the hub, the plurality of expandable members extending from hub, each member having a collapsed configuration for insertion into the vessel and for subsequent removal from the vessel and an expanded configuration where at least a portion of the expandable member contacts a distinct portion of an inner surface of the tubular graft to expand that portion of the graft.

8. The device for repairing the vessel of the body of claim 7, where at least one of the plurality of expandable members comprises a hook at a free end of the member.

9. The device for repairing the vessel of the body of claim 7, where:
   at least one permanent stent is disposed within the tubular graft;
   at least one of the plurality of expandable members has a convex curve towards the longitudinal axis followed by a concave curve away from the longitudinal axis;
   at least one of the plurality of expandable members comprises a hook at a free end of the member; and
   at least one member connecting two or more frame units.

10. The device for repairing the vessel of the body in claim 7, where the at least one of the plurality of expandable members has a convex curve towards the longitudinal axis followed by a concave curve away from the longitudinal axis.

11. The device for repairing the vessel of the body in claim 7, further comprising two or more frame units coupled together by a connecting member.

12. A device for repairing a vessel of a body, comprising:
    a tubular graft having a proximal end, a distal end, and a lumen therethrough, the graft having a collapsed configuration for delivery into the vessel and an expanded configuration for at least partially engaging the vessel, where the graft comprises a biocompatible material capable of incorporation into the vessel wall; and
    a plurality of distinct and independently insertable, positionable, and expandable frame units removably disposed within the lumen of the tubular graft, each frame unit having an expanded configuration and a collapsed configuration, a proximal end and a distal end,
    where each frame unit comprises a plurality of expandable members extending from a hub defined by a longitudinal axis, and at least a portion of the expandable members in the expanded configuration contacts a distinct portion of an inner surface of the tubular graft to expand that portion of the graft, where at least one expandable member has a convex curve towards the longitudinal axis followed by a concave curve away from the longitudinal axis; and
    where each frame unit is repositionable within the tubular graft or removable from the tubular graft.

13. The device for repairing the vessel of the body in claim 12, where two or more of the frame units are removably coupled together by a connecting member.

14. The device for repairing the vessel of the body of claim 12, where at least one of the plurality of expandable members comprises a hook at a free end of the at least one member.

15. The device for repairing the vessel of the body of claim 12, where each of the plurality of expandable members has a diameter in the range of about 0.010 inches to about 0.050 inches.

16. The device for repairing the vessel of the body of claim 12, further comprising at least one permanent stent disposed within the tubular graft.

17. The device of repairing the vessel of the body of claim 12, where each frame unit further comprises a capture mechanism at the distal end configured to engage a device for removing the frame unit from the graft.

18. The device of repairing the vessel of the body of claim 12, wherein the hub has a first face and a second face and the plurality of expandable members extends only from the first face of the hub.

* * * * *